United States Patent
Pang et al.

(10) Patent No.: US 12,276,589 B1
(45) Date of Patent: Apr. 15, 2025

(54) METHOD AND SYSTEM FOR DETECTING OIL ABRASIVE PARTICLE SIZE

(71) Applicants: Taiyuan University of Technology, Taiyuan (CN); Shanxi KEDA AUTOMATION CONTROL Co., Ltd., Taiyuan (CN)

(72) Inventors: Xinyu Pang, Taiyuan (CN); Shijie Cui, Taiyuan (CN); Mingyuan Guo, Taiyuan (CN); Kaibo Lv, Taiyuan (CN); Feng Li, Taiyuan (CN); Xuewen Wang, Taiyuan (CN); Yan Wu, Taiyuan (CN); Yong'ai Cao, Taiyuan (CN); Pengfeng Shao, Taiyuan (CN); Yuewei Wang, Taiyuan (CN); Jiawei Bai, Taiyuan (CN); Yixiang He, Taiyuan (CN)

(73) Assignees: Taiyuan University of Technology, Taiyuan (CN); Shanxi KEDA AUTOMATION CONTROL co., Ltd., Taiyuan (CN)

( * ) Notice: Subject to any disclaimer, the term of this patent is extended or adjusted under 35 U.S.C. 154(b) by 0 days.

(21) Appl. No.: 18/961,577

(22) Filed: Nov. 27, 2024

(30) Foreign Application Priority Data

Nov. 27, 2023 (CN) .......................... 202311598217.2

(51) Int. Cl.
*G01N 15/02* (2024.01)
*G01N 33/28* (2006.01)

(52) U.S. Cl.
CPC ..... *G01N 15/0266* (2013.01); *G01N 33/2858* (2013.01)

(58) Field of Classification Search
CPC .................. G01N 33/2858; G01N 15/0266
See application file for complete search history.

(56) References Cited

PUBLICATIONS

CNIPA, Office Action, Application No. 202311598217.2, Jun. 14, 2024.
Jia et al: "Theory and Applications of Machine Olfaction Technology", Shaanxi Xinhua Publishing & Media, Jun. 16, 2024.
Niu et al: "Design of Inductive Sensor System for Wear Particles in Oil", Journal of Mechanical Engineering, vol. 57, No. 12, p. 126-135, Jun. 2021.

*Primary Examiner* — Alesa Allgood
*Assistant Examiner* — Courtney G McDonnough
(74) *Attorney, Agent, or Firm* — WCF IP

(57) ABSTRACT

Provided are a method and system for detecting an oil abrasive particle size. The method includes: acquiring a voltage signal of an oil abrasive particle in real time, where the voltage signal is generated in real time in a process that the oil abrasive particle passes through an electromagnetic abrasive particle sensor; establishing a voltage curve coordinate system with an amplitude of the voltage signal as a Y-axis and a time of the voltage signal as an X-axis, and obtaining a voltage curve; performing feature extraction on the voltage curve, and obtaining an area S defined by a voltage curve within a half voltage signal cycle T and the X-axis and a maximum absolute value A of a voltage signal value according to the voltage curve coordinate system; and inputting S and A to a trained back propagation neural network for prediction to obtain a predicted oil abrasive particle size.

8 Claims, 5 Drawing Sheets

---

Step 1: acquire a voltage signal of an oil abrasive particle in real time, where the voltage signal is generated in real time in a process that the oil abrasive particle passes through an electromagnetic abrasive particle sensor Step 2: establish a voltage curve coordinate system with an amplitude of the voltage signal as a Y-axis and a time of the voltage signal as an X-axis Step 3: perform feature extraction on the voltage curve, and obtain an area S defined by a voltage curve within a half voltage signal cycle T and the X-axis and a maximum absolute value A of a voltage signal value according to the voltage curve coordinate system Step 4: input A and S to a trained BP neural network for prediction to obtain a predicted oil abrasive particle size Step 1: acquire a voltage signal of an oil abrasive particle in real time, where the voltage signal is generated in real time in a process that the oil abrasive particle passes through an electromagnetic abrasive particle sensor Step 2: establish a voltage curve coordinate system with an amplitude of the voltage signal as a Y-axis and a time of the voltage signal as an X-axis Step 3: perform feature extraction on the voltage curve, and obtain an area S defined by a voltage curve within a half voltage signal cycle T and the X-axis and a maximum absolute value A of a voltage signal value according to the voltage curve coordinate system Step 4: input A and S to a trained BP neural network for prediction to obtain a predicted oil abrasive particle size

FIG. 1

| 1 | Peak | Area s | Radius |
|---|---|---|---|
| 2 | 0.3306 | 1.2955 | 0.05 |
| 3 | 10.05 | 39.386 | 0.1 |
| 4 | 75.16 | 294.59 | 0.15 |
| 5 | 306.7 | 1202.3 | 0.2 |
| 6 | 878.1 | 3444 | 0.25 |
| 7 | 1965 | 7711.3 | 0.3 |
| 8 | 3643 | 14307 | 0.35 |
| 9 | 5830 | 22913 | 0.4 |

| 1 | Peak | Area s | Actual Radius | Predicted Radius | Error |
|---|---|---|---|---|---|
| 2 | 12460 | 49179 | 0.53 | 0.5552 | 4.70% |
| 3 | 17260 | 68416 | 0.63 | 0.5983 | -5% |
| 4 | 21420 | 85440 | 0.73 | 0.74 | 1.40% |

METHOD AND SYSTEM FOR DETECTING OIL ABRASIVE PARTICLE SIZE

CROSS REFERENCE TO RELATED APPLICATION

This patent application claims the benefit and priority of Chinese Patent Application No. 2023115982172, filed with the China National Intellectual Property Administration on Nov. 27, 2023, the disclosure of which is incorporated by reference herein in its entirety as part of the present application.

TECHNICAL FIELD

The present disclosure relates to the technical field of fault diagnosis, and in particular, to a method and system for detecting an oil abrasive particle size.

BACKGROUND

The gear drive device may produce a plurality of metallic and non-metallic abrasive particles due to frictional abrasion in the operating process. These abrasive particles are mostly present in lubricating oil in a suspended state. Researches have showed that feature information (such as the size, the quantity, and the material) of metallic abrasive particles produced by abrasion is closely related to whether the operating state of a mechanical device is good. Under normal circumstances, abrasive particles produced by normal abrasion have a size of less than 60 microns. When abnormal abrasion that might cause a major accident occurs in the mechanical device, 70-500 micron abrasive particles may be produced. These particles will travel along with the oil inside the device, causing problems of abnormal abrasion, crushing and scratching, fatigue, heating and the like of parts, and even leading to device shutdown and causing an enterprise to suspend production in severe cases.

There are currently a plurality of sensor products available on the market, in which the single-channel electromagnetic abrasive particle sensor and the sensor product capable of detecting metallic abrasive particles having an equivalent diameter of less than 100 microns are common. Also, the multimode array sensor designed for the large-diameter oil line is very popular, which can not only realize full-flow area detection, but also can detect tiny abrasive particles. However, the multimode array sensor is a combination of a plurality of coil sensors, and since the magnetic field produced by a single sensor has a wide range of action, the electromagnetic interference may be generated in the array sensor. Even abrasive particles of a same size pass through different array sensor channels from central axes at the same speed, output signals may have a significant difference so that the sensor cannot accurately determine the size of the particles.

In most existing researches, the shielding structure is added between array sensor structures to reduce the electromagnetic interference. On the one hand, the complexity of the sensor manufacturing process is increased; and on the other hand, the electromagnetic interference cannot be completely eliminated by the shielding structure and may still have an impact on detection signals.

SUMMARY

An objective of embodiments of the present disclosure is to provide a method and system for detecting an oil abrasive particle size to improve the accuracy of abrasive particle detection.

To achieve the above objective, the embodiments of the present disclosure provide the following technical solutions.

A method for detecting an oil abrasive particle size includes:
acquiring a voltage signal of an oil abrasive particle in real time, where the voltage signal is generated in real time in a process that the oil abrasive particle passes through an electromagnetic abrasive particle sensor;
establishing a voltage curve coordinate system with an amplitude of the voltage signal as a Y-axis and a time of the voltage signal as an X-axis, and obtaining a voltage curve;
performing feature extraction on the voltage curve, and obtaining an area S defined by a voltage curve within a half voltage signal cycle T and the X-axis and a maximum absolute value A of a voltage signal value according to the voltage curve coordinate system; and
inputting the area S and the maximum absolute value A of the voltage signal value to a trained back propagation (BP) neural network for prediction to obtain a predicted oil abrasive particle size.

Optionally, that the voltage signal is generated in real time in a process that the oil abrasive particle passes through an electromagnetic abrasive particle sensor may specifically include:
for a single-channel electromagnetic abrasive particle sensor, place oil abrasive particles that have different sizes at a central axis of the channel for uniform linear motion, and put abrasive particles of a same size in uniform linear motion once, thereby generating different voltage signals;
or,
for a multimode arrayed electromagnetic abrasive particle sensor arranged in a square shape or circumferentially, obtain a center of symmetry B of a combined shape of all channels according to sections perpendicular to central axes of the channels; classify all channels of which the central axes have an equal distance to the center of symmetry B as channels of a same class; classify multimode arrayed channels corresponding to the channels of the same class as a group of channels, where channels in a same group of channels have a consistent inner diameter size; select any channel in any group of channels, place oil abrasive particles that have different sizes at the central axis of the channel for uniform linear motion, and put abrasive particles of a same size in uniform linear motion once, thereby generating different voltage signals.

Optionally, the establishing a BP neural network model may include:
dividing different voltage signals of any group of channels into a training set and a test set;
extract a maximum absolute value A1 of a voltage signal value and an area S1 defined by a voltage curve within a half voltage signal cycle T and an X-axis in the training set; and extract a maximum absolute value A2 of the voltage signal value and an area S2 defined by the voltage curve within the half voltage signal cycle T and the X-axis in the test set;
inputting the maximum absolute value A1 of the voltage signal value and the area S1 to a neural network model for training to obtain a corresponding BP neural network, where each group of channels corresponds to one BP neural network model; and
inputting the maximum absolute value A2 of the voltage signal value and the area S2 to the BP neural network for testing to obtain a test result and optimizing the BP neural network according to the test result.

Optionally, establishing the BP neural network further may further include:

determining a number of neurons of a hidden layer of the BP neural network, where a specific formula is as follows:

$$l=\sqrt{m+n}+\alpha;$$

where l represents a number of nodes of the hidden layer; m represents a number of input nodes; n represents a number of output nodes; and a is a constant in a range of 1 to 10.

Optionally, the inputting the maximum absolute value A2 of the voltage signal value and the area S2 to the BP neural network for testing to obtain a test result and optimizing the BP neural network according to the test result may specifically include:

an error range of the test result being±5%; and a goodness of fit of the BP neural network being greater than or equal to 0.995.

A system for detecting an oil abrasive particle size includes:

a signal acquisition unit configured to acquire a voltage signal of an oil abrasive particle in real time, where the voltage signal is generated in real time in a process that the oil abrasive particle passes through an electromagnetic abrasive particle sensor;

a voltage curve establishment unit connected with the signal acquisition unit and configured to establish a voltage curve coordinate system with an amplitude of the voltage signal as a Y-axis and a time of the voltage signal as an X-axis, and obtain a voltage curve;

a feature extraction unit connected with the voltage curve establishment unit and configured to perform feature extraction on the voltage curve, and obtain an area S defined by a voltage curve within a half voltage signal cycle T and the X-axis and a maximum absolute value A of a voltage signal value according to the voltage curve coordinate system; and a BP neural network unit connected with the feature extraction unit and configured to input the area S and the maximum absolute value A of the voltage signal value to a trained BP neural network for prediction to obtain a predicted oil abrasive particle size.

Optionally, the signal acquisition unit may include:

a signal generation module configured to:

for a single-channel electromagnetic abrasive particle sensor, place oil abrasive particles that have different sizes at a central axis of the channel for uniform linear motion, and put abrasive particles of a same size in uniform linear motion once, thereby generating different voltage signals;

or, for a multimode arrayed electromagnetic abrasive particle sensor arranged in a square shape or circumferentially, obtain a center of symmetry B of a combined shape of all channels according to sections perpendicular to central axes of the channels; classify all channels of which the central axes have an equal distance to the center of symmetry B as channels of a same class; classify multimode arrayed channels corresponding to the channels of the same class as a group of channels, where channels in a same group of channels have a consistent inner diameter size; select any channel in any group of channels, place oil abrasive particles that have different sizes at the central axis of the channel for uniform linear motion, and put abrasive particles of a same size in uniform linear motion once, thereby generating different voltage signals.

Optionally, the BP neural network unit may include:

a classification module configured to divide different voltage signals of any group of channels into a training set and a test set;

an extraction module configured to:

extract a maximum absolute value A1 of a voltage signal value and an area S1 defined by a voltage curve within a half voltage signal cycle T and an X-axis in the training set; and extract a maximum absolute value A2 of the voltage signal value and an area S2 defined by the voltage curve within the half voltage signal cycle T and the X-axis in the test set;

an input module configured to input the maximum absolute value A1 of the voltage signal value and the area S1 to a neural network model for training to obtain a corresponding BP neural network, where each group of channels corresponds to one BP neural network model; and an optimization module configured to input the maximum absolute value A2 of the voltage signal value and the area S2 to the BP neural network for testing to obtain a test result and optimize the BP neural network according to the test result.

Optionally, the BP neural network unit may further include:

a neuron number determination module configured to determine a number of neurons of a hidden layer of the BP neural network, where a specific formula is as follows:

$$l=\sqrt{m+n}+\alpha;$$

where l represents a number of nodes of the hidden layer; m represents a number of input nodes; n represents a number of output nodes; and a is a constant in a range of 1 to 10.

Optionally, the optimization module may include:

an error determination submodule configured to determine whether an error range of the test result is ±5%; and a goodness-of-fit determination submodule configured to determine whether a goodness of fit of the BP neural network is greater than or equal to 0.995.

In the embodiments of the present disclosure, a voltage signal of an oil abrasive particle is acquired in real time, and the oil abrasive particles may generate a voltage signal when passing through a pipe filled with the oil. The problem of a difference between signals produced by the same abrasive particles passing through different channels due to an electromagnetic interface between the channels of a multimode arrayed electromagnetic abrasive particle sensor is overcome. A voltage curve coordinate system is established with an amplitude of the voltage signal as a Y-axis and a time as an X-axis. Feature extraction is performed on the voltage curve, and an area S defined by a voltage curve within a half voltage signal cycle T and the X-axis and a maximum absolute value A of a voltage signal value are obtained according to the voltage curve coordinate system; and S and A are input to a trained BP neural network for prediction to obtain a predicted oil abrasive particle size. The accuracy of abrasive particle detection is improved.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other drawings can be derived from these accompanying drawings by those of ordinary skill in the art without creative efforts.

FIG. 1 is a flowchart of a method for detecting an oil abrasive particle size provided by an embodiment of the present disclosure;

Figure 2:
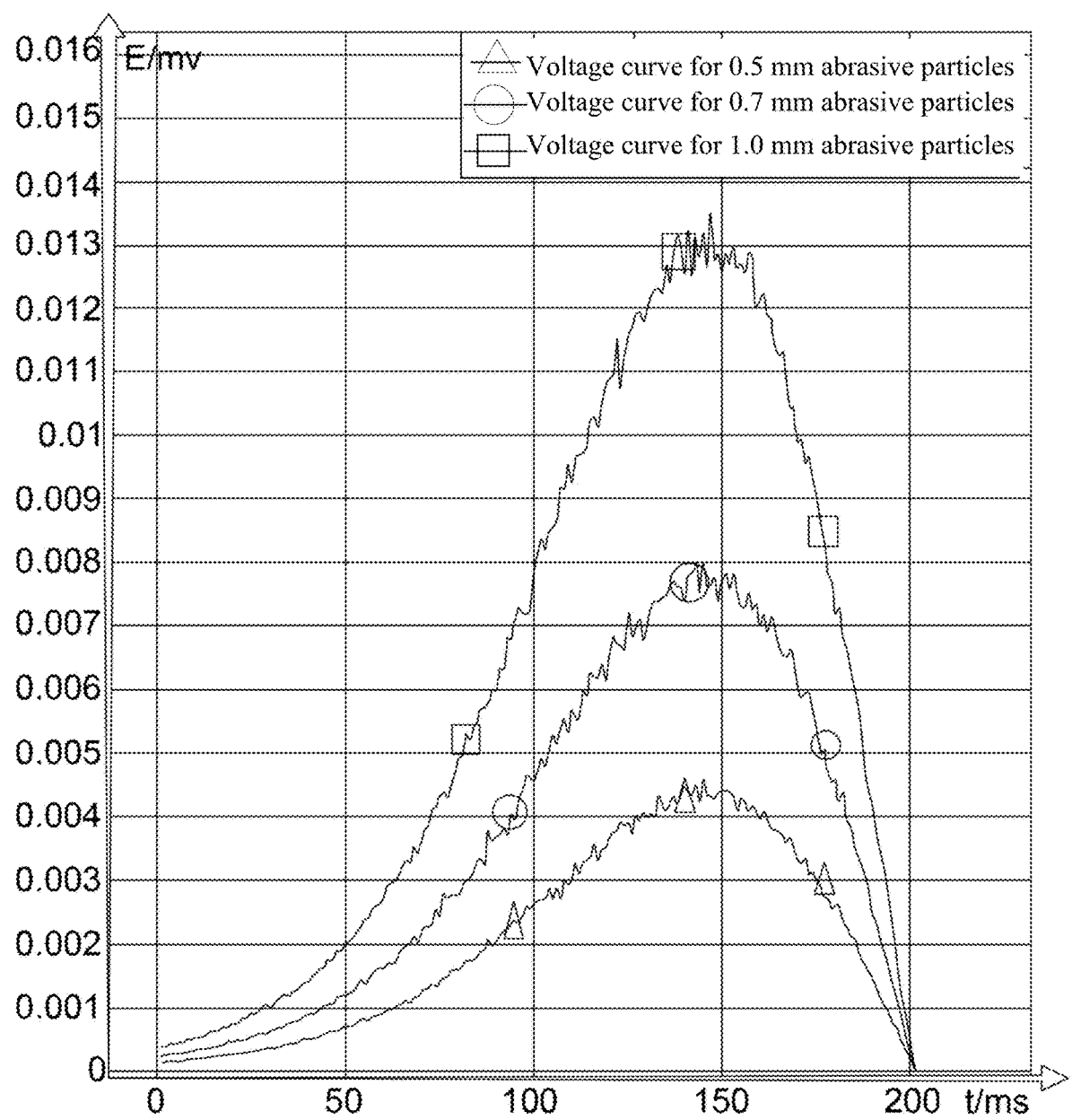
FIG. 2 is a schematic diagram of a voltage curve coordinate system provided by an embodiment of the present disclosure.

REFERENCE NUMERALS signal acquisition unit—1, voltage curve establishment unit—2, feature extraction unit—3, and BP neural network unit—4.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments derived from the embodiments of the present disclosure by those skilled in the art without creative efforts shall fall within the protection scope of the present disclosure.

An objective of the present disclosure is to provide a method and system for detecting an oil abrasive particle size to solve the existing problem of low accuracy of abrasive particle detection.

To make the above objective, features, and advantages of the present disclosure clearer and more comprehensible, the present disclosure will be further described in detail below with reference to the accompanying drawings and the specific examples.

FIG. 1 illustrates an exemplary flow of a method for detecting an oil abrasive particle size mentioned above. Steps are described in detail below.

In step 1, a voltage signal of an oil abrasive particle is acquired in real time, and the voltage signal is generated when the oil abrasive particle passes through a pipe filled with the oil. Specific steps are as follows.

In step 11, for a single-channel electromagnetic abrasive particle sensor, oil abrasive particles that have different sizes are placed at a central axis of the channel for uniform linear motion, and abrasive particles of a same size are put in uniform linear motion once, thereby generating different voltage signals;

or, for a multimode arrayed electromagnetic abrasive particle sensor arranged in a square shape or circumferentially, a center of symmetry B of a combined shape of all channels is obtained according to sections perpendicular to central axes of the channels; all channels of which the central axes have an equal distance to the center of symmetry B are classified as channels of a same class; multimode arrayed channels corresponding to the channels of the same class are classified as a group of channels, where channels in a same group of channels have a consistent inner diameter size; any channel in any group of channels is selected; oil abrasive particles that have different sizes are placed at the central axis of the channel for uniform linear motion, and abrasive particles of a same size are put in uniform linear motion once, thereby generating different voltage signals.

In an example, in step 1, the voltage signal of the oil abrasive particles can be acquired in real time using a sensor for abrasive particles in oil. The sensor for abrasive particles in oil may be a single-channel single-coil, two-coil or three-coil electromagnetic abrasive particle sensor.

The oil abrasive particles having different sizes are placed at a central axis of the pipe filled with the oil for uniform linear motion, and abrasive particles of a same size are put in uniform linear motion once. This process may be achieved by fixing the abrasive particles on a conveyor belt. Voltage signals of the oil abrasive particles passing through the pipe at the fixed speed are then detected by the sensor for abrasive particles in oil, thereby obtaining a plurality of sample datasets including the voltage signals. The sample datasets are then divided into a training set and a test set according to a data ratio of 8:2.

In another example, referring to FIG. 2, a multi-channel multimode arrayed electromagnetic sensor for abrasive particles in oil arranged in a square shape or circumferentially is used. A center of symmetry B of a combined shape of all channels is obtained on sections perpendicular to central axes of the channels; all channels of which the central axes have an equal distance to the point B are classified as a same class, and multimode arrayed channels corresponding to the same class are classified as a group of channels, labeled as group 1, group 2, etc., where channels in a same group have a consistent inner diameter size. Any channel in any group is selected; oil abrasive particles that have different sizes are placed at the central axis of the channel for uniform linear motion, and abrasive particles of a same size are put in uniform linear motion once, thereby generating different voltage signals. For other groups, any channel in any group may be selected for operations according to the same steps.

Figure 7:
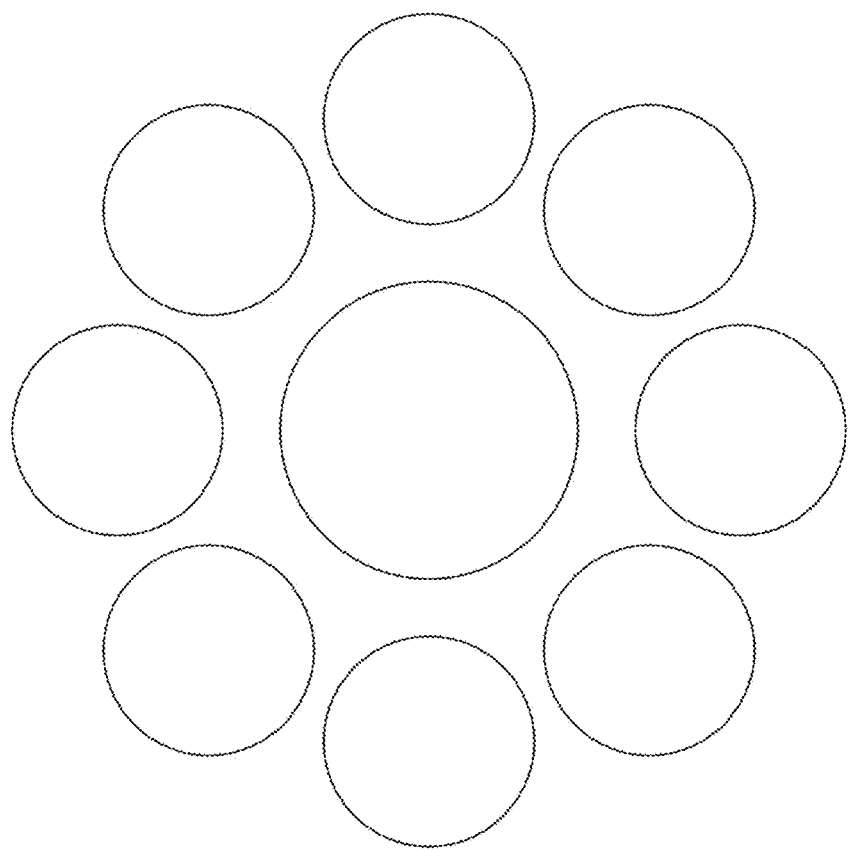
FIG. 7 is a front view of a circumferential 9-channel multimode arrayed electromagnetic abrasive particle sensor according to an embodiment of the present disclosure.

Taking a 3×3 square multimode arrayed sensor for abrasive particles in oil as an example, there are 3 groups, and there is no sequential order for the groups. These groups include 4 channels, 4 channels, and 1 channel, respectively. Referring to FIG. 7, the steps are described by taking a circumferential 9-channel multimode arrayed sensor for abrasive particles in oil as an example. From the above description, there are only two groups, where group 1 has 8 multimode arrayed channels and group 2 only has 1 channel. Any channel in group 1 is selected. A plurality of abrasive particles of known sizes are sequentially placed at the central axis of the pipe for uniform linear motion, where a speed is a flow velocity of the oil under a working condition; the sizes of the abrasive particles are different, range from 5 to 500 microns, and are distributed as uniformly as possible. The number of the abrasive particles cannot be less than 10, or otherwise, it may affect the compensation accuracy. Only one abrasive particle is allowed to pass through each time. This process can be achieved by fixing the abrasive particles on a synchronous belt or a traction fiber. The voltage signals of the oil abrasive particles passing through the pipe at the speed are then recorded, finally obtaining a plurality of sample datasets including the voltage signals. The sample datasets are then divided into a training set and a test set according to a ratio of 8:2. The same steps are performed for group 2, and the sample datasets are also divided into a training set and a test set according to the ratio of 8:2.

In step 2, a voltage curve coordinate system is established with an amplitude of the voltage signal as a Y-axis and a time of the voltage signal as an X-axis, and a voltage curve is obtained.

Referring to FIG. 2, the X-axis is time, in units of millisecond. The Y-axis is the amplitude of the voltage signal, in units of millivolt. A distance between two most adjacent zero-point horizontal coordinates of the voltage curve is a half cycle T.

In step 3, feature extraction is performed on the voltage curve, and an area S defined by a voltage curve within a half voltage signal cycle T and the X-axis and a maximum absolute value A of a voltage signal value are obtained according to the voltage curve coordinate system.

Figures 3, 4, 5:
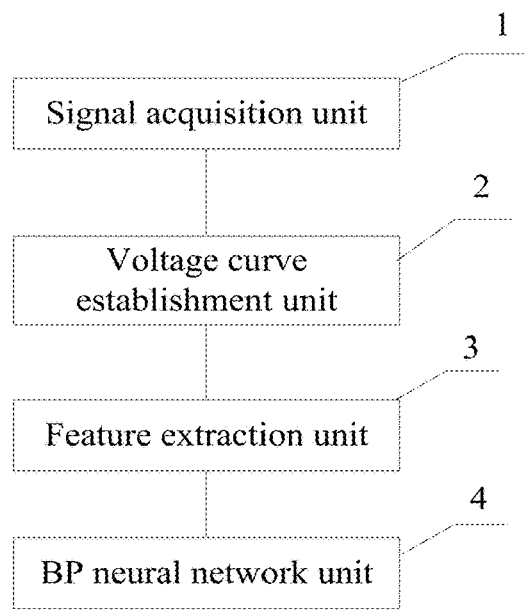
FIG. 3 is a diagram illustrating data of a maximum absolute value A of a voltage signal value, a corresponding area A, and a predicted size of an oil abrasive particle provided by an embodiment of the present disclosure.
FIG. 4 is a diagram illustrating error range data of a test result provided by an embodiment of the present disclosure.
FIG. 5 is a schematic structural diagram of a system for detecting an oil abrasive particle size provided by an embodiment of the present disclosure.

In one example, feature extraction is performed on the voltage curves of the training set and the test set. Referring to FIG. 3, an area S defined by a voltage curve and a 'zero voltage coordinate axis', namely the area S defined by the voltage curve within the half voltage signal cycle T and the X-axis, can be achieved by importing voltage signal data into Matlab software. The defined area S is obtained by firstly executing code 'data=dlmread('Untitled1.txt'); x=data(:,2); y=data(:,3); figure(2); plot(x,y); z=trapz(x,y) % area'. The maximum absolute value A of the voltage signal value can be obtained by a data statistics maximum option.

In step 4, the area S and the maximum absolute value A of the voltage signal value are input to a trained BP neural network for prediction to obtain a predicted oil abrasive particle size.

In one example, the maximum absolute value A of the voltage signal value and the corresponding area S are used as two input layer neurons to the BP neural network, and the predicted oil abrasive particle size corresponding to the maximum absolute value A of the voltage signal value is used as an output layer neuron. The BP neural network model includes one input layer and one output layer.

Referring to FIG. 4, there is shown a diagram illustrating data of the maximum absolute value A (peak value) of the voltage signal value, the corresponding area A, and the predicted size (radius) of the oil abrasive particles.

Establishing the BP neural network includes the following steps.

In step 41, different voltage signals of any group of channels are divided into a training set and a test set.

In step 42, a maximum absolute value A1 of a voltage value and an area S1 defined by a voltage curve within a half voltage signal cycle T and an X-axis in the training set are extracted; and a maximum absolute value A2 of the voltage signal value and an area S2 defined by the voltage curve within the half voltage signal cycle T and the X-axis in the test set are extracted.

In step 43, the maximum absolute value A1 of the voltage signal value and the area S1 are input to a neural network model for training to obtain a corresponding BP neural network, where each group of channels corresponds to one BP neural network model.

In step 44, the maximum absolute value A2 of the voltage signal value and the area S2 are input to the BP neural network for testing to obtain a test result and the BP neural network is optimized according to the test result. Specific steps are as follows.

An error range of the test result is ±5%; and

A goodness of fit of the BP neural network is greater than or equal to 0.995.

In one example, referring to FIG. 4, an actual size (actual radius) of the oil abrasive particles is subtracted from the predicted size (predicted radius) of the oil abrasive particles to obtain an error; a proportion of the error in the actual radius is calculated, guaranteeing that a proportion range is less than or equal to +5%. The goodness of fit of the BP neural network should be above 0.995.

In another example, the set BP neural network is trained. The data of group 1 and group 2 should be trained separately, so as to obtain training models having an error within a target error range of 5% and a goodness of fit above 0.995. Thus, the two training models can be utilized to identify the oil abrasive particles online. A abrasive particle within a range of 5 to 500 microns is arbitrarily selected and caused to pass through the sensor in the same way, and the absolute value A of the voltage signal thereof is measured. If the abrasive particle passes through the channel of group 1, the absolute value is input to the trained model of group 1, or otherwise input to the trained model of group 2. After prediction, a result D is output, namely a compensated abrasive particle size.

Establishing the BP neural network further includes the following steps.

In step 45, a number of neurons of a hidden layer of the BP neural network is determined, where a specific formula is as follows:

$$1=\sqrt{m+n}+\alpha;$$

where 1 represents a number of nodes of the hidden layer; m represents a number of input nodes; n represents a number of output nodes; and a is a constant in a range of 1 to 10.

Figure 6:
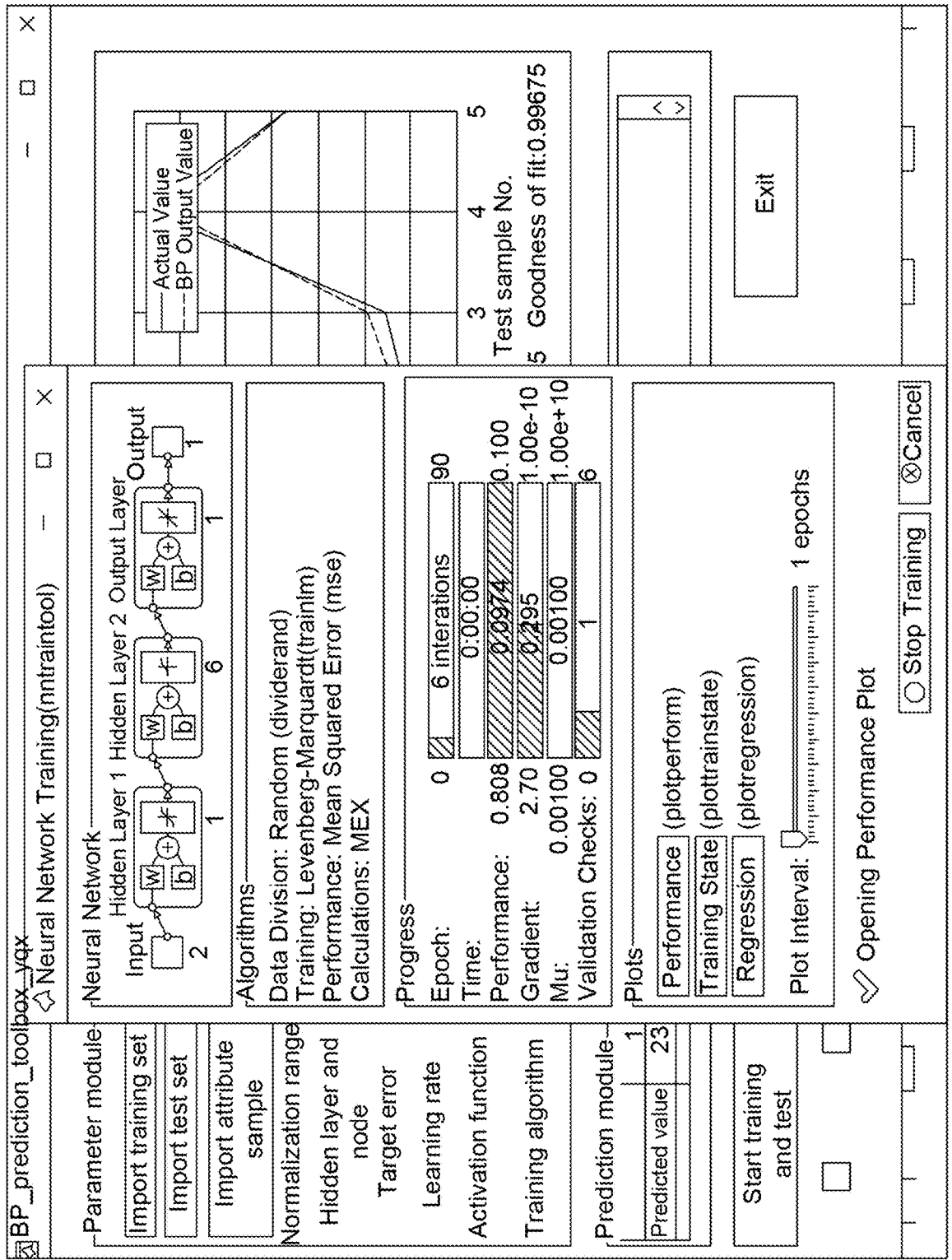
FIG. 6 illustrates a group of trained BP neural network models according to an embodiment of the present disclosure.

In one example, referring to FIG. 6, the structure of the BP neural network is designed to establish a 3-layer BP neural network including 1 hidden layer, including 1 input layer neuron and 1 output layer neuron. After repeated testing, a number of hidden layer nodes is set to 2. A neuron transfer function for a hidden layer is S type log function log sig, and a neuron transfer function for an output layer is a linear function purelin. The BP neural network is trained using Trainlm function, and a learning rate is determined to be 0.1, and a target error to $1 \times 10^{-6}$, and a maximum number of generations to 99. A momentum coefficient is 0.9 so that the BP neural network algorithm can be avoided from local minimum and the learning speed can be increased.

In conclusion, in the embodiments of the present disclosure, oil abrasive particles may generate a voltage signal in real time in a process of passing through an electromagnetic abrasive particle sensor; a voltage curve coordinate system is established with an amplitude of the voltage signal as a Y-axis and a time of the voltage signal as an X-axis, and a voltage curve is obtained; feature extraction is performed on the voltage curve, and an area S defined by a voltage curve within a half voltage signal cycle T and the X-axis and a maximum absolute value A of a voltage signal value are obtained according to the voltage curve coordinate system;

and the area S and the absolute value A of the voltage signal value are input to a trained BP neural network in a corresponding group for prediction to obtain a predicted oil abrasive particle size. A difference between signals produced by the same abrasive particles passing through different channels due to an electromagnetic interface between the channels of a multimode arrayed electromagnetic abrasive particle sensor can be well eliminated. In addition, for a single-channel sensor, the area S and the absolute value A of the voltage signal value are both used as inputs to the neural network. Compared with the traditional dependence that a maximum absolute value of a voltage signal value is in positive correlation to the third power of a radius of abrasive particles, the accuracy of abrasive particle detection can be improved.

According to the structure of the sensor used, information may be extracted from an obtained abrasive particle signal after grouping according to steps for training the BP neural network model. Meanwhile, the method provided in the present disclosure only involves one hidden layer such that the model training time is greatly reduced. Experimental results prove that the accuracy of the oil abrasive particle size measured by the method provided in the present disclosure is above 95%. The method has the characteristics of high accuracy, high identification speed, etc.

To achieve the above objective, the embodiments of the present disclosure further provide the following technical solutions.

A system for detecting an oil abrasive particle size, with reference to FIG. 5, includes the following units.

A signal acquisition unit 1 is configured to acquire a voltage signal of an oil abrasive particle in real time, where the voltage signal is generated in real time in a process that the oil abrasive particle passes through an electromagnetic abrasive particle sensor.

The signal acquisition unit 1 includes: a signal generation module.

The signal generation module is configured to, for a single-channel electromagnetic abrasive particle sensor, place oil abrasive particles that have different sizes at a central axis of the channel for uniform linear motion, and put abrasive particles of a same size in uniform linear motion once, thereby generating different voltage signals;

or, for a multimode arrayed electromagnetic abrasive particle sensor arranged in a square shape or circumferentially, obtain a center of symmetry B of a combined shape of all channels according to sections perpendicular to central axes of the channels; classify all channels of which the central axes have an equal distance to the center of symmetry B as channels of a same class; classify multimode arrayed channels corresponding to the channels of the same class as a group of channels, where channels in a same group of channels have a consistent inner diameter size; select any channel in any group of channels, place oil abrasive particles that have different sizes at the central axis of the channel for uniform linear motion, and put abrasive particles of a same size in uniform linear motion once, thereby generating different voltage signals.

A voltage curve establishment unit 2 is connected with the signal acquisition unit 1. The voltage curve establishment unit 2 is configured to establish a voltage curve coordinate system with an amplitude of the voltage signal as a Y-axis and a time of the voltage signal as an X-axis, and obtain a voltage curve.

A feature extraction unit 3 is connected with the voltage curve establishment unit 2. The feature extraction unit 3 is configured to perform feature extraction on the voltage curve and obtain an area S defined by a voltage curve within a half voltage signal cycle T and the X-axis and a maximum absolute value A of a voltage signal value according to the voltage curve coordinate system.

A BP neural network unit 4 is connected with the feature extraction unit 3. The BP neural network unit 4 is configured to input the area S and the maximum absolute value A of the voltage signal value to a trained BP neural network for prediction to obtain a predicted oil abrasive particle size.

The BP neural network unit includes:

a classification module configured to divide different voltage signals of any group of channels into a training set and a test set;

an extraction module configured to:

extract a maximum absolute value A1 of a voltage signal value and an area S1 defined by a voltage curve within a half voltage signal cycle T and an X-axis in the training set; and extract a maximum absolute value A2 of the voltage signal value and an area S2 defined by the voltage curve within the half voltage signal cycle T and the X-axis in the test set;

an input module configured to input the maximum absolute value A1 of the voltage signal value and the area S1 to a neural network model for training to obtain a corresponding BP neural network, where each group of channels corresponds to one BP neural network model; and an optimization module configured to input the maximum absolute value A2 of the voltage signal value and the area S2 to the BP neural network for testing to obtain a test result and optimize the BP neural network according to the test result.

The optimization module includes:

an error determination submodule configured to determine whether an error range of the test result is ±5%; and a goodness-of-fit determination submodule configured to determine whether a goodness of fit of the BP neural network is greater than or equal to 0.995.

The BP neural network unit further includes:

a neuron number determination module configured to determine a number of neurons of a hidden layer of the BP neural network, where a specific formula is as follows:

$$l = \sqrt{m+n} + \alpha;$$

where l represents a number of nodes of the hidden layer; m represents a number of input nodes; n represents a number of output nodes; and a is a constant in a range of 1 to 10.

The embodiments are described herein in a progressive manner. Each embodiment focuses on the difference from another embodiment, and the same and similar parts between the embodiments may refer to each other. Since the system disclosed in the embodiments corresponds to the method disclosed in the embodiments, the description is relatively simple, and reference can be made to the method description.

Specific examples are used herein for illustration of principles and embodiments of the present disclosure. The descriptions of the above embodiments are merely used for assisting in understanding the methods and core ideas of the embodiments of the present disclosure. In addition, those of ordinary skill in the art can make various modifications in terms of the particular implementations and the scope of application in accordance with the ideas of the present disclosure. In conclusion, the content of the description shall not be construed as limitations to the embodiments of the present disclosure.

What is claimed is:

1. A method for detecting an oil abrasive particle size, comprising:
acquiring a voltage signal of an oil abrasive particle in real time, wherein the voltage signal is generated in real time in a process that the oil abrasive particle passes through an electromagnetic abrasive particle sensor, specifically comprising:
for a multimode arrayed electromagnetic abrasive particle sensor arranged in a square shape or circumferentially, obtaining a center of symmetry B of a combined shape of all channels according to sections perpendicular to central axes of the channels; classifying all channels of which the central axes have an equal distance to the center of symmetry B as channels of a same class; classifying multimode arrayed channels corresponding to the channels of the same class as a group of channels, wherein channels in a same group of channels have a consistent inner diameter size; selecting any channel in any group of channels, placing oil abrasive particles that have different sizes at the central axis of the channel for uniform linear motion, and putting abrasive particles of a same size in uniform linear motion once, thereby generating different voltage signals;
establishing a voltage curve coordinate system with an amplitude of the voltage signal as a Y-axis and a time of the voltage signal as an X-axis, and obtaining a voltage curve;
performing feature extraction on the voltage curve, and obtaining an area S defined by a voltage curve within a half voltage signal cycle T and the X-axis and a maximum absolute value A of a voltage signal value according to the voltage curve coordinate system; and
inputting the area S and the maximum absolute value A of the voltage signal value to a trained back propagation (BP) neural network for prediction to obtain a predicted oil abrasive particle size.

2. The method for detecting an oil abrasive particle size according to claim 1, wherein the establishing a BP neural network model comprises:
dividing different voltage signals of any group of channels into a training set and a test set;
extracting a maximum absolute value A1 of a voltage signal value and an area S1 defined by a voltage curve within a half voltage signal cycle T and an X-axis in the training set; extracting a maximum absolute value A2 of the voltage signal value and an area S2 defined by the voltage curve within the half voltage signal cycle T and the X-axis in the test set;
inputting the maximum absolute value A1 of the voltage signal value and the area S1 to a neural network model for training to obtain a corresponding BP neural network, wherein each group of channels corresponds to one BP neural network model; and
inputting the maximum absolute value A2 of the voltage signal value and the area S2 to the BP neural network for testing to obtain a test result and optimizing the BP neural network according to the test result.

3. The method for detecting an oil abrasive particle size according to claim 2, wherein establishing the BP neural network further comprises:

determining a number of neurons of a hidden layer of the BP neural network according to the following formula:

$$l=\sqrt{m+n}+a;$$

wherein l represents a number of nodes of the hidden layer; m represents a number of input nodes; n represents a number of output nodes; and a is a constant in a range of 1 to 10.

4. The method for detecting an oil abrasive particle size according to claim 3, wherein the inputting the maximum absolute value A2 of the voltage signal value and the area S2 to the BP neural network for testing to obtain a test result and optimizing the BP neural network according to the test result specifically comprise:
an error range of the test result being ±5%; and
a goodness of fit of the BP neural network being greater than or equal to 0.995.

5. A system for detecting an oil abrasive particle size, comprising:
a signal acquisition unit configured to acquire a voltage signal of an oil abrasive particle in real time, wherein the voltage signal is generated in real time in a process that the oil abrasive particle passes through an electromagnetic abrasive particle sensor, specifically comprising:
a signal generation module configured to:
for a multimode arrayed electromagnetic abrasive particle sensor arranged in a square shape or circumferentially, obtain a center of symmetry B of a combined shape of all channels according to sections perpendicular to central axes of the channels; classify all channels of which the central axes have an equal distance to the center of symmetry B as channels of a same class; classify multimode arrayed channels corresponding to the channels of the same class as a group of channels, wherein channels in a same group of channels have a consistent inner diameter size; select any channel in any group of channels, place oil abrasive particles that have different sizes at the central axis of the channel for uniform linear motion, and put abrasive particles of a same size in uniform linear motion once, thereby generating different voltage signals;
a voltage curve establishment unit connected with the signal acquisition unit and configured to establish a voltage curve coordinate system with an amplitude of the voltage signal as a Y-axis and a time of the voltage signal as an X-axis, and obtain a voltage curve;
a feature extraction unit connected with the voltage curve establishment unit and configured to perform feature extraction on the voltage curve, and obtain an area S defined by a voltage curve within a half voltage signal cycle T and the X-axis and a maximum absolute value A of a voltage signal value according to the voltage curve coordinate system; and
a BP neural network unit connected with the feature extraction unit and configured to input the area S and the maximum absolute value A of the voltage signal value to a trained BP neural network for prediction to obtain a predicted oil abrasive particle size.

6. The system for detecting an oil abrasive particle size according to claim 5, wherein the BP neural network unit comprises:
a classification module configured to divide different voltage signals of any group of channels into a training set and a test set;
an extraction module configured to:

extract a maximum absolute value A1 of a voltage signal value and an area S1 defined by a voltage curve within a half voltage signal cycle T and an X-axis in the training set; and extract a maximum absolute value A2 of the voltage signal value and an area S2 defined by the voltage curve within the half voltage signal cycle T and the X-axis in the test set;

an input module configured to input the maximum absolute value A1 of the voltage signal value and the area S1 to a neural network model for training to obtain a corresponding BP neural network, wherein each group of channels corresponds to one BP neural network model; and an optimization module configured to input the maximum absolute value A2 of the voltage signal value and the area S2 to the BP neural network for testing to obtain a test result and optimize the BP neural network according to the test result.

7. The system for detecting an oil abrasive particle size according to claim 6, wherein the BP neural network unit further comprises:

a neuron number determination module configured to determine a number of neurons of a hidden layer of the BP neural network according to the following formula:

$$l=\sqrt{m+n}+\alpha;$$

wherein l represents a number of nodes of the hidden layer; m represents a number of input nodes; n represents a number of output nodes; and a is a constant in a range of 1 to 10.

8. The system for detecting an oil abrasive particle size according to claim 7, wherein the optimization module comprises:

an error determination submodule configured to determine whether an error range of the test result is ±5%; and a goodness-of-fit determination submodule configured to determine whether a goodness of fit of the BP neural network is greater than or equal to 0.995.

* * * * *